United States Patent [19]

Mitsui et al.

[11] Patent Number: 4,678,861

[45] Date of Patent: Jul. 7, 1987

[54] PROCESS FOR PRODUCING A CYCLOOLEFIN

[75] Inventors: Osamu Mitsui; Yohei Fukuoka, both of Kurashiki, Japan

[73] Assignee: Asahi Kasei Kogyo Kabushiki Kaisha, Osaka, Japan

[21] Appl. No.: 790,521

[22] Filed: Oct. 23, 1985

[51] Int. Cl.$^4$ .......................... C07C 5/10; C07C 5/11
[52] U.S. Cl. ................................. 585/266; 585/269; 585/271; 585/273
[58] Field of Search ................ 585/266, 269, 271, 273

[56] References Cited

U.S. PATENT DOCUMENTS

| | | | |
|---|---|---|---|
| 3,274,272 | 9/1966 | Amagass et al. | 585/269 |
| 3,321,539 | 5/1967 | Slaugh | 585/269 |
| 3,391,206 | 7/1968 | Hartog | 585/269 |
| 3,767,720 | 10/1973 | Drinkard | 585/269 |
| 4,197,415 | 4/1980 | Hideyuki et al. | 585/269 |
| 4,495,373 | 1/1985 | Niwa et al. | 585/269 |

FOREIGN PATENT DOCUMENTS

| | | |
|---|---|---|
| 37-31929 | 7/1962 | Japan . |
| 40-48724 | 8/1965 | Japan . |
| 47-42645 | 12/1972 | Japan . |
| 49-51596 | 11/1975 | Japan . |
| 51-98243 | 8/1976 | Japan . |
| 53-46939 | 4/1978 | Japan . |
| 59-184138 | 10/1984 | Japan ................................. 585/269 |
| 662538 | 5/1979 | U.S.S.R. ............................ 585/269 |

OTHER PUBLICATIONS

Encyclopedia Chemica, vol. 2, p. 755, (1963).
Odenbrand et al, "*Hydrogenation of Benzene to Cyclohexene on a Ruthenium Catalyst: Influence of Some Reaction Parameters*", J. Chem. Tech. Biotechnol., 1980, 30, 677–687.

Primary Examiner—Asok Pal
Attorney, Agent, or Firm—Birch, Stewart, Kolasch & Birch

[57] ABSTRACT

A process for producing a cycloolefin which comprises partially hydrogenating a monocyclic aromatic hydrocarbon in the presence of a ruthenium catalyst composed of a rare earth element compound solid carrier and a ruthenium component supported thereon. The resulting cycloolefin is obtained in high yield and high selectivity and the catalyst can be repeatedly used for a prolonged period of time.

29 Claims, No Drawings

PROCESS FOR PRODUCING A CYCLOOLEFIN

This invention relates to a process for producing a cycloolefin. More particularly, the present invention is concerned with a process for producing a cycloolefin in which the partial hydrogenation of a monocyclic aromatic hydrocarbon is effected in the presence of a specific ruthenium catalyst so that the corresponding cycloolefin is obtained in high yield and high selectivity. By the process of the present invention, various valuable cycloolefins can be advantageously produced on a commercial scale.

A cycloolefin is an important compound to be used for the production of various valuable compounds. Hitherto a cycloolefin such as cyclohexene has been produced from a monocyclic aromatic hydrocarbon through complicated multiple steps. For example, cyclohexene has been produced by a method in which benzene is hydrogenated to cyclohexane and the resulting cyclohexane is subjected to air oxidation to obtain cyclohexanol, followed by dehydration of the resulting cyclohexanol. Another method of producing cyclohexene consists in halogenating benzene, hydrogenating the resulting product to obtain a halogenated cyclohexane and dehydrohalogenating the obtained halogenated cyclohexane. Because the above mentioned methods for producing a cycloolefin require complicated multiple steps, the efficiencies of such methods are poor, thus leading to high production cost for producing the cycloolefin.

A number of methods have been proposed with respect to the preparation of a cycloolefin by partial hydrogenation of benzene. This is because the preparation of a cycloolefin by partial hydrogenation of benzene which requires only a single step is considered to be advantageous. Examples of methods of producing a cycloolefin by partial hydrogenation of benzene are as follows, (1) a method in which the hydrogenation is carried out in a medium of liquid ammonia in the presence of an alkali metal (U.S. Pat. Nos. 3,274,272 and 3,321,539 and Japanese Patent Application Publication Specification Nos. 40-6864, 40-6865 and 43-8102); (2) a method in which the hydrogenation is carried out using ruthenium as a catalyst and a lower alcohol as a solvent (U.S. Pat. No. 3,391,206); (3) a method in which the hydrogenation is carried out using a ruthenium catalyst in the presence of an aqueous neutral or acid solution containing a chloride or sulfate salt of a Group Ia metal, a Group IIa metal, Mn, Zn or ammonia (Japanese Patent Application Laid-Open Specification No. 5198243); (4) a method in which the hydrogenation is carried out in the presence of a ruthenium catalyst and an aqueous solution of a carbonate or a basic carbonate of cobalt, nickel or copper (Japanese Patent Application Laid-Open Specification No. 53-46939); and (5) a method in which the hydrogenation is carried out using as a catalyst a reduced cation of at least one member selected from the Group VIII elements of the Periodic Table in the presence of water and an alkaline agent (U.S. Pat. No. 3,767,720).

However, none of the above-mentioned conventional methods are satisfactory from a practical point of view. For instance, according to the method (1), a cycloolefin can advantageously be produced in relatively high yield but the method requires recovery of the used liquid ammonia and alkali metal. The methods (2) to (4) are not advantageous in that the selectivity for cycloolefin is low. In the method (5) a cycloolefin can be obtained in relatively high yield but this method has the following serious drawbacks. Specifically, the relatively high yield of the cycloolefin in the method (5) is attributable to the combined use of a large amount of alkali and an additive selected from various metal compounds, e.g., carbonyl compounds of chrominum or other metals. However, due to the presence of a large amount of alkali and the above-mentioned additive in the reaction system, the rate of hydrogenation is extremely low, requiring the hydrogenation reaction to be continued for a prolonged period of time. Moreover, the presence of alkali and anions coming from the additives at high concentrations causes the corrosion of the reactor to be highly accelerated. Therefore, a reactor made of a corrosion resistant material should be used. In the method (5), when the hydrogenation reaction is effected in the absence of the above-mentioned additives, the rate of hydrogenation is slightly increased but the selectivity for cycloolefin is significantly lowered. Further, in the method (5), the active ingredient of the catalyst may be used in a form which is supported on various carriers. However, the solid carriers used in the method (5) tend to dissolve in the aqueous alkali during the hydrogenation reaction, and thereafter deposit onto the catalyst to lowering the catalytic activity of the said catalyst. Therefore, because of the instability of the solid carrier the catalyst used in the method (5) cannot be repeatedly used and cannot be used for a long period of time. In view of the above, the method (5) has not been regarded as an advantageous method from a commercial point of view.

As is apparent from the foregoing, no conventional methods of producing a cycloolefin are suitable for the production of a cycloolefin on a commercial scale.

The present inventors have made extensive and intensive studies for the purpose of developing a catalyst for the production of a cycloolefin, which enables a cycloolefin to be advantageously produced by partial hydrogenation of the corresponding monocyclic aromatic hydrocarbon on a commercial scale. As a result, the present inventors have surprisingly found that if a ruthenium catalyst composed of a solid carrier and, supported thereon, a ruthenium component is prepared using a solid carrier comprising a rare earth element compound, the resulting ruthenium catalyst has a prolonged life and, in addition, is effective for producing a cycloolefin in high selectivity and high yield. The present invention has been made based on such a novel discovery.

Accordingly, it is an object of the present invention to provide a process for producing a cycloolefin by partial hydrogenation of a monocyclic aromatic hydrocarbon in the presence of a catalyst, which can produce a cycloolefin not only in high yield but also in high selectivity.

The foregoing and other objects, features and advantages of the present invention will be apparent to those skilled in the art from the following detailed description and appended claims.

In accordance with the present invention, there is provided a process for producing a cycloolefin which comprises partially hydrogenating a monocyclic aromatic hydrocarbon in the presence of a ruthenium catalyst composed of a solid carrier and a ruthenium component supported thereon, said solid carrier comprising at least one rare earth element compound.

The catalyst to be used in the process according to the present invention is composed of a solid carrier and a ruthenium component supported thereon. In the catalyst, it is essential that the solid carrier should comprise at least one rare earth element compound. The term "rare earth element" as used in the present invention is intended to mean the lanthanide elements, i.e., lanthanum (La), cerium (Ce), praseodymium (Pr), neodymium (Nd), promethium (Pm), samarium (Sm), europium (Eu), gadolinium (Gd), terbium (Tb), dysprosium (Dy), holminum (Ho), erbium (Er), thulium (Tm), ytterbium (Yb) and lutecium (Lu); and scandium (Sc) and yttrium (Y). It is preferred that the rare earth element be one member selected from the group consisting of Sc, La, Ce, Tb and Yb. Of the above-mentioned elements, La is more preferable. As examples of the suitable rare earth element compound, there may be mentioned at least one member selected from the group consisting of oxides, hydroxides, carbonates and phosphates of a rare earth element. Of these, oxides, hydroxides and carbonates of a rare earth element are more preferable because they can be stably present in the reaction system, contributes to a high selectivity for the intended cyclohexene and are easily available. Especially preferred are oxides and hydroxides of a rare earth element because anions originating from the compounds cause no corrosion of the reactor, they are excellent in stability, i.e. the ruthenium component supported on the compounds does not peel therefrom, and they contribute to a high selectivity for the intended cycloolefin. More especially preferred is one member selected from the group consisting of oxides and hydroxides of La.

Further, the rare earth element compound may be an oxide compound composed of an oxide of a rare earth element and an oxide of at least one metal other than the rare earth element. Preferable oxide compounds are ones selected from the group consisting of one composed of an oxide of Al and an oxide of La and one composed of an oxide of Zn and an oxide of La. The oxide compound can be prepared according to the customary method for example, as follows. The salts of the metals are dissolved in water. Then, an aqueous alkali solution is added to the metal salt solution, so that the metals coprecipitate in the form of hydroxides. The resulting metal hydroxides are then calcined to obtain a compound oxide. Alternatively, in some cases, a compound oxide may be produced by simply calcining a mixture of hydroxides or oxides of the metals. The oxide compound composed of an oxide of a rare earth element and a metal oxide other than the oxide of a rare earth element may be produced in various atomic ratios of the rare earth element to the metal other than the rare earth element. For example, a compound oxide composed of lanthum oxide and zinc oxide may be produced in a La/Zn atomic ratio of 1:1 to 9:1.

As mentioned before, the solid carrier of the catalyst to be used in the present invention comprises at least one rare earth element compound. A preferred composition of the solid carrier may comprise (a) 30 to 100 mol%, more preferably 50 to 100 mol%, based on the total molar amount of the components (a) and (b), of at least one rare earth element compound and (b) 70 to 0 mol%, more preferably 50 to 0 mol%, based on the total molar amount of the components (a) and (b), of at least one metal compound other than the rare earth element compound. As the component (a), any of the above-mentioned rare earth element compounds may be used. As the component (b) there may be used any metal compound other than the rare earth element compound. When the component (b) comprises a catalyst poison such as iron oxide and arsenic oxide, it is preferred that the amount of the catalyst poison be less than 1:10 in terms of the atomic ratio of the metal component of the catalyst poison to the ruthenium supported on the solid carrier. Further, when the hydrogenation reaction of a monocyclic aromatic hydrocarbon is effected in an alkaline solution in the presence of the present catalyst, a component (b) material which tends to dissolve in the alkaline solution such as $Al_2O_3$ and $Cu_2O$, are incorporated. It is preferred that the amount of such material be 30 mol% or less based on the total molar amount of the components (a) and (b).

The solid carrier of the catalyst of the present invention may contain any metal and carbon as far as they do not exert an adverse effect on the selectivity for and the yield of the intended cycloolefin.

Incidentally, with respect to the solid carrier of the catalyst to be used in the present invention, it is noted that sandy ores (about 200 μm) such as monazite, bastinaesite and xenotime which are raw materials of rare earth element compounds generally comprise about 30 mol % or more of rare earth element compounds and the balance of metal compounds which may be used as the above-mentioned component (b). Therefore, such ores, in the form as such, may be used as the solid carrier.

The content of the ruthenium component in the catalyst to be used in the present invention is preferably 0.01 to 10 wt %, more preferably 0.1 to 5 wt %, in terms of ruthenium element, based on the carrier. In this connection, it is noted that part or all of the ruthenium component may be present in the form of metallic ruthenium. The content of the ruthenium component in the catalyst may be determined by emission spectroanalysis using an inductively coupled plasma equipment (JY-38PII, manufactured and sold by Seiko Denshi Kogyo K.K., Japan).

The source of the ruthenium component is not critical, and any compounds may be used as far as they can be supported on a solid carrier comprising at least one rare earth element compound. For example, as the source of the ruthenium component, there may be mentioned a chloride, bromide or nitrate of ruthenium.

The catalyst to be used in the present invention may be prepared according to the customary methods, for example, impregnation method, vaporization-dryness method and precipitation method.

The thus obtained catalyst may be subjected to a treatment with a reducing agent such as hydrogen, sodium borohydride, hydrazine and formalin to activate the catalyst. The treatment with hydrogen in the vapor phase is extremely useful for this purpose. Of course, the catalyst may be used as is without a preliminary treatment with a reducing agent. In this case, the catalyst is automatically activated by the action of hydrogen used during the hydrogenation of a monocyclic aromatic hydrocarbon.

The monocyclic aromatic hydrocarbon to be used in the present invention is preferably benzene, toluene, o-xylene, m-xylene, p-xylene and ethylbenzene, more preferably benzene.

In practicing the present invention, the partial hydrogenation (hereinafter often referred to simply as "hydrogenation") of a monocyclic aromatic hydrocarbon may be carried out in the absence of a solvent. However, it is preferred that the hydrogenation be carried out in the presence of water or an alcohol to increase the rate of hydrogenation and the selectivity for cycloolefin. It is especially preferred to effect the hydrogenation reaction in the presence of water. In this connection, the water may generally be present in an amount of 0.01 to 100 times by weight of the amount of a monocyclic aromatic hydrocarbon to be used. The preferred amount of water is in the range of 0.5 to 20 times by weight of the amount of a monocyclic aromatic hydrocarbon, because the presence of too much water requires the use of a reactor having a large capacity and, at the same time, causes the selectivity for cycloolefin to be lowered.

When the hydrogenation of a monocyclic hydrocarbon is effected in the presence of water, it is preferred that water be used in the form of aqueous solutions of a salts, such as chlorides, sulfates, carbonates and phosphates and hydroxides as in conventional known methods (Japanese Patent Application Laid-Open Specification Nos. 47-42645, 50-142536 and 51-98243). In this connection, it is especially preferred that the hydrogenation of a monocyclic aromatic hydrocarbon be effected in the copresence of water and an alkaline agent. Such copresence is effective for further improvement in selectivity for the intended cycloolefin. The term "alkaline agent" as used herein is intended to mean one which in water gives an aqueous solution having a pH value greater than 7.5. As examples of the alkaline agent, there may be mentioned hydroxides, oxides and carbonates of metals of the Groups Ia and IIa of the Periodic Table, i.e., lithium, sodium, potassium, rubidium, cesium, calcium, strontium and barium; ammonia; and water-soluble organic bases, e.g. alkylmonoamines, e.g., methylamine, dimethylamine and diethylamine, alkylenediamines, e.g. ethylenediamine and propylenediamine, pyridine and quaternary ammonium salts. The alkaline agents may be used alone or in combination of two or more. Of them, preferred are hydroxides, oxides and carbonates of Li, Na, K, Rb and Ce.

In general, when the concentration of the alkaline agent is high, the rate of hydrogenation of a monocyclic aromatic hydrocarbon is lowered. On the other hand, when the concentration of the alkaline agent is low, the extent of the improvement in selectivity for the intended cycloolefin is small. Therefore, it is preferred that water and the alkaline agent constitute an aqueous solution having an alkaline agent concentration of 0.01 to 10 mol/liter, more preferably 0.1 to 5 mol/liter.

In the present invention, if desired, the hydrogenation of a monocyclic aromatic hydrocarbon may be effected in the copresence of at least one cation selected from the group consisting of $Ca^{2+}$, $Zn^{2+}$, $Cu^+$, $Cu^{2+}$, $Cr^{3+}$, $Ni^{2+}$, $Co^{2+}$, $Fe^{2+}$, $Fe^{3+}$, $Mo^{2+}$, $Al^{3+}$, $Mg^{2+}$, $Hg^{2+}$, $Hg^+$ and $Ti^{3+}$, preferably $Zn^{2+}$ and $Al^{3+}$, more preferably $Zn^{2+}$. The above-mentioned cations may be added to the reaction system as an auxiliary compound in the form of a compound selected from chlorides, bromides, fluorides, sulfates, nitrates, phosphates, carbonates, organic acid salts, oxides and hydroxides. Of them, an oxide and hydroxide of Zn are especially preferable. The auxiliary compound may be used in an amount of 0.01 to 20 mol %, in terms of ruthenium element, based on the amount of the ruthenium component of the catalyst.

In general, the above-mentioned auxiliary compound is separately added to the reaction system. However, when a zinc compound is used as auxiliary compound, the zinc compound may be incorporated into the solid carrier of the catalyst. Further, as mentioned above, the zinc compound may be used in the form of an oxide compound composed of zinc oxide and an oxide of a rare earth element.

When the hydrogenation reaction is carried out in the presence of water, the above-mentioned auxiliary compound may be used in the form of an aqueous solution.

The process of the present invention may generally be effected continuously or batch-wise in a liquid suspension system or in a fixed bed system. When the hydrogenation reaction is effected in a liquid suspension system, a monocyclic aromatic hydrocarbon, a catalyst and any additives are put in a sealed vessel and hydrogen gas is then introduced into the vessel to effect the hydrogenation of the monocyclic aromatic hydrocarbon. Alternatively, a mixture of a monocyclic aromatic hydrocarbon, a catalyst and any additives is passed together with hydrogen gas through a tubular reactor. On the other hand, the hydrogenation reaction is effected in a fixed bed system, a catalyst is packed in a column and a monocyclic aromatic hydrocarbon is fed to the column together with any additives and hydrogen gas to effect the hydrogenation of the monocyclic aromatic hydrocarbon.

The reaction conditions may vary according to the kind and amount of the catalyst and any additives used. However, in general, when both the reaction temperature and the reaction pressure are low, both the conversion of a monocyclic aromatic hydrocarbon and the selectivity for the intended cycloolefin are decreased. On the other hand, when both the reaction temperature and the reaction pressure are high, the conversion of a monocyclic aromatic hydrocarbon is increased but the selectivity for the cycloolefin is decreased. Therefore, the hydrogen pressure is generally 1 to 200 $kg/cm^2$ G, preferably 10 to 100 $kg/cm^2$G, and the reaction temperature is generally 20° to 250° C., preferably 100° to 200° C.

When the reaction is effected in the liquid suspension system, the amount of the catalyst is generally 0.001 to 50 % by weight based on the amount of the monocyclic aromatic hydrocarbon, preferably 0.01 to 20 % by weight.

When the reaction is effected in a fixed bed system, the liquid hourly space velocity (LHSV) is generally 0.001 to 100 liter/liter/hr, preferably 0.01 to 50 liter/liter/hr.

The reaction time is not critical, and the reaction may be effected for several seconds to several hours.

As described in the foregoing, the process of the present invention is extremely useful for the preparation of a cycloolefin on a commercial scale. Specifically, according to the present invention, the intended cycloolefin can be prepared not only in a high yield but also in a high selectivity by virtue of the use of a specific ruthenium catalyst comprising a ruthenium component and a solid carrier supporting thereon the ruthenium component and comprising at least one rare earth element compound. Further, the catalyst to be used in the process of the present invention has a prolonged catalyst life. This is attributable to an excellent stability of the solid carrier of the catalyst. Specifically, conventional ruthenium catalysts contain as solid carrier zeolites or alumina. Therefore, when the hydrogenation of a monocyclic aromatic hydrocarbon is effected in the copresence of the conventional catalyst and an aqueous solution of an alkaline agent, the solid carrier of the catalyst tends to be dissolved in the alkaline solution during the hydrogenation reaction, causing the activity of the catalyst to be rapidly decreased. On the other hand, the solid carrier of the catalyst to be used in the process of the present invention contains at least one rare earth element compound. The solid carrier comprising at least one rare earth element has a low solubility in an alkaline solution and, hence, can be stably present in an alkaline solution during the hydrogenation reaction. Because of the excellent stability of the solid carrier of the catalyst, the catalyst to be used in the process of the present invention can be repeatedly used for a prolonged period of time. Therefore, the yield of the intended cycloolefin per unit weight of ruthenium contained in the catalyst is remarkably improved as compared with the conventional ruthenium catalyst in which a zeolite or alumina is used as the solid carrier.

The present invention will now be described in detail with reference to the following Examples that are by no means limiting the scope of the present invention.

In Examples, the conversion of a monocyclic aromatic hydrocarbon, selectivity for a cycloolefin and yield of a cycloolefin are those obtained by the following formula:

Conversion of a monocyclic aromatic hydrocarbon (%) = (1)

$$\frac{\text{(mole number of consumed monocyclic aromatic hydrocarbon)}}{\text{(mole number of fed monocyclic aromatic hydrocarbon)}} \times 100$$

Selectivity for a cycloolefin (%) = (2)

$$\frac{\text{(mole number of produced cycloolefin)}}{\text{(mole number of consumed monocyclic aromatic hydrocarbon)}}$$

Yield of a cycloolefin (%) = (3)

$$\frac{\text{(mole number of produced cycloolefin)}}{\text{(mole number of fed monocyclic aromatic hydrocarbon)}}$$

EXAMPLE 1

A ruthenium catalyst was prepared as follows. $RuCl_3.3H_2O$ (manufactured and sold by Nippon Engelhard Ltd., Japan) was dissolved in water to obtain an aqueous solution containing 0.006 wt % of ruthenium. In 2,000 ml of the aqueous solution was dispersed 20 g of lanthanum oxide powder (purity: more than 99%) (manufactured and sold by Wako Pure Chemical Industries Ltd., Japan) to be used as a solid carrier. The resulting mixture was stirred for 3 hours and allowed to stand. The adsorption of ruthenium on lanthanum oxide was confirmed by the disappearance of the dark brown color of ruthenium. The mixture was then subjected to filtration. The obtained solid was dried in vacuo (20 mmHg) at 80° C. for 6 hours to obtain a dried powder. 10 g of the obtained powder was dispersed in 100 ml of water placed in a 200 ml-three neck flask. Nitrogen gas was flushed into the flask. 1 g of $NaBH_4$ was then added with nitrogen gas flush. The resulting mixture was stirred for 1 hour. Then the mixture was filtered, and the residue was washed with water in an atmosphere of nitrogen gas, and dried in vacuo (20 mmHg) at 80° C. for 6 hours to obtain a catalyst containing 0.6 wt %, in terms of ruthenium element and based on the solid carrier, of the ruthenium component.

3.9 g the thus obtained catalyst and 200 ml of benzene was charged in a stainless steel (SUS316) autoclave (capacity: 1 liter) equipped with a stirrer. The atmosphere in the autoclave was replaced by the nitrogen gas. The temperature of the contents was elevated to 155° C. while stirring. After elevation of the temperature, hydrogen gas was fed into the autoclave, and the contents were kept at 175° C. under a pressure of 50 kg/cm²G for 15 minutes to effect a hydrogenation reaction.

Thereafter, the contents of the autoclave were cooled rapidly, and the organic layer was taken out of the autoclave and subjected to analysis by means of gas chromatography. As a result, it was found that the conversion of benzene was 14.4 % and that the selectivity for cyclohexene was 6.3 %. Beside the desired cyclohexene, there was observed formation of cyclohexane.

COMPARATIVE EXAMPLE 1

A hydrogenation reaction was carried out in substantially the same manner as in Example 1, except that 24 mg of ruthenium black (manufactured and sold by Nippon Engelhard Ltd., Japan) was used as a catalyst and that the reaction was effected for 60 minutes. In spite of the long reaction period (60 min.), the conversion of benzene was as low as 11.5 % and the selectivity for cyclohexene also was as low as 2.5 %.

From the above results, it is understood that by the use of a ruthenium catalyst comprising ruthenium supported on lanthanum oxide, both the rate of hydrogenation and the selectivity for cyclohexene can be improved.

EXAMPLES 2 to 4

Substantially the same procedures as in Example 1 were repeated to effect hydrogenation reactions, except that the reaction time was changed as indicated in Table 1 given below and that the hydrogenation reaction was effected in the presence of 400 ml of water. The results are shown in Table 1.

COMPARATIVE EXAMPLES 2 to 4

Substantially the same procedures as in Examples 2 to 4 were repeated to effect hydrogenation reactions, except that 61 mg of $RuCl_3.3H_2O$ was used instead of the catalyst used in Examples 2 to 4 and that the reaction time was changed as indicated in Table 1 given below. The results are shown in Table 1.

TABLE 1

| Examples | Water (ml) | Reaction time (minutes) | Conversion of benzene (%) | Selectivity for cyclohexene (%) | Yield of cyclohexene (%) |
|---|---|---|---|---|---|
| Example 2 | 400 | 5 | 41.2 | 23.5 | 9.7 |
| Example 3 | " | 10 | 65.4 | 16.4 | 10.7 |
| Example 4 | " | 15 | 79.7 | 9.7 | 7.7 |
| Comparative Example 2 | " | 2 | 30.6 | 5.7 | 1.7 |
| Comparative Example 3 | " | 5 | 56.4 | 2.4 | 1.4 |
| Comparative Example 4 | " | 8 | 80.0 | 1.0 | 0.8 |

As is apparent from Table 1, the presence of water in the reaction system is effective for increasing not only the rate of hydrogenation of benzene but also the selectivity for cyclohexene. It is also understood from Table 1 that when a catalyst comprising ruthenium supported on lanthanum oxide is used in the presence of water, the rate of hydrogenation is low but the selectivity for cyclohexene is high, leading to a high yield of cyclohexene, as compared with the case where a ruthenium catalyst having no support is used.

EXAMPLES 5 to 29

Ruthenium catalysts were prepared in substantially the same manner as in Example 1, except that solid carriers as indicated in Table 2 given below were used instead of lanthanum oxide. 5 g of the catalyst was charged into an autoclave equipped with a stirrer together with 100 ml of benzene, 400 ml of water and 30 g of NaOH. The hydrogenation reaction was carried out in substantially the same manner as in Example 1 under a reaction pressure of 50 kg/cm$^2$G at a reaction temperaturere of 175° C. The results are shown in Table 2.

TABLE 2

| Examples | Solid carrier | Reaction time (minutes) | Conversion of benzene (%) | Selectivity for cyclohexene (%) | Yield of cyclohexene (%) |
|---|---|---|---|---|---|
| Example 5 | La$_2$O$_3$[1] | 5 | 12.3 | 71.5 | 8.8 |
| Example 6 | " | 15 | 27.8 | 63.7 | 17.7 |
| Example 7 | " | 30 | 40.3 | 54.6 | 22.0 |
| Example 8 | Tm$_2$O$_3$[2] | 5 | 15.0 | 38.0 | 10.1 |
| Example 9 | " | 10 | 62.6 | 32.3 | 20.2 |
| Example 10 | Yb$_2$O$_3$[2] | 5 | 17.8 | 59.1 | 10.5 |
| Example 11 | " | 15 | 51.7 | 32.8 | 17.3 |
| Example 12 | Tb$_4$O$_7$[2] | 2 | 17.4 | 58.2 | 10.1 |
| Example 13 | " | 5 | 40.8 | 48.3 | 19.7 |
| Example 14 | " | 10 | 70.4 | 17.6 | 12.4 |
| Example 15 | CeO$_2$[3] | 5 | 16.4 | 53.2 | 8.7 |
| Example 16 | " | 12 | 38.9 | 36.2 | 18.5 |
| Example 17 | " | 20 | 62.4 | 23.7 | 14.8 |
| Example 18 | Y$_2$O$_3$[4] | 30 | 26.0 | 42.3 | 11.0 |
| Example 19 | " | 60 | 31.2 | 40.1 | 12.5 |
| Example 20 | Rare earth oxide[5] | 15 | 15.7 | 60.1 | 9.4 |
| Example 21 | Rare earth oxide[5] | 30 | 30.8 | 52.3 | 16.1 |
| Example 22 | Rare earth oxide[5] | 60 | 59.2 | 32.3 | 17.1 |
| Example 23 | Sm$_2$O$_3$[2] | 3 | 21.9 | 45.3 | 9.9 |
| Example 24 | " | 6 | 40.5 | 32.1 | 13.0 |
| Example 25 | " | 12 | 65.3 | 17.0 | 11.1 |
| Example 26 | Dy$_2$O$_3$[2] | 10 | 32.1 | 38.3 | 12.3 |
| Example 27 | Nd$_2$O$_3$[2] | " | 49.1 | 25.3 | 12.4 |
| Example 28 | Pr$_6$O$_{11}$[2] | " | 48.3 | 25.2 | 12.2 |
| Example 29 | Eu$_2$O$_3$[2] | " | 49.1 | 32.3 | 15.9 |

Note:
[1]La$_2$O$_3$: manufactured and sold by Santoku Kinzoku, Japan; the grade for optical lens; purity, more than 99.99%
[2]Yb$_2$O$_3$, Tb$_4$O$_7$, Sm$_2$O$_3$, Dy$_2$O$_3$, Nd$_2$O$_3$, Pr$_6$O$_{11}$, Eu$_2$O$_3$: manufactured and sold by Wako Pure Chemical Industry, Ltd., Japan; purity, more than 99.9%
[3]CeO$_2$: manufactured and sold by Shinnihon Kinzoku, Japan; purity, more than 99.6%
[4]Y$_2$O$_3$: manufactured and sold by Wako Bussan, Japan; purity, more than 60%
[5]Rare earth oxide: manufactured and sold by Shinnihon Kinzoku, Japan; purity (total of rare earth), 81.5% (CeO$_2$ content: 70.2%)

COMPARATIVE EXAMPLES 5 to 13

Ruthenium catalysts were prepared in substantially the same manner as in Example 5, except that solid carriers as indicated in Table 3 given below were used instead of La$_2$O$_3$. The hydrogenation reactions of benzene were effected in substantially the same manner as in Example 5, except that the above-obtained catalysts were used instead of the catalyst used in Example 5. The results are shown in Table 3.

TABLE 3

| Examples | Solid carrier | Reaction time (minutes) | Conversion of benzene (%) | Selectivity for cyclohexene (%) | Yield of cyclohexene (%) |
|---|---|---|---|---|---|
| Comparative Example 5 | Al$_2$O$_3$[6] | 5 | 12.8 | 30.0 | 3.8 |
| Comparative Example 6 | " | 15 | 25.3 | 25.9 | 6.6 |
| Comparative Example 7 | " | 30 | 59.1 | 11.2 | 6.6 |
| Comparative Example 8 | Active carbon[7] | 5 | 9.2 | 5.4 | 0.5 |
| Comparative Example 9 | Active carbon[7] | 15 | 27.2 | 1.8 | 0.5 |
| Comparative Example 10 | Active carbon[7] | 30 | 55.8 | 0.5 | 0.3 |
| Comparative Example 11 | SK-40[8] | 5 | 13.8 | 25.2 | 3.5 |
| Comparative Example 12 | " | 15 | 39.2 | 8.5 | 3.3 |
| Comparative Example 13 | " | 30 | 74.1 | 5.4 | 4.0 |

Note:
[6]Al$_2$O$_3$: KHA-24, manufactured and sold by Nishio Kogyo, Japan
[7]Active carbon: Beads Carbon-LP, manufactured and sold by Taiyo Kaken
[8]SK-40: a Y-type zeolite manufactured and sold by Union Carbide Corp., USA

EXAMPLE 30

The hydrogenation of benzene was effected in the same manner as in Example 7. The results were the same as those of Example 7. After completion of the reaction, the organic layer was taken out of the autoclave, and 100 ml of fresh benzene was placed in the autoclave. The hydrogenation reaction was carried out under a pressure of 50 Kg/cm$^2$G at 175° C. for 30 minutes. The above-mentioned procedures were repeated. The results of the fifth hydrogenation reaction were substantially the same as those of the first hydrogenation reaction, that is, the conversion of benzene was 38.4 %, the selectivity for cyclohexene was 56.0 % and the yield of cyclohexene was 21.5 %.

EXAMPLES 31 to 41

The hydrogenation reactions conducted in Examples 9, 11, 14, 17, 18, 22, 25, 26, 27, 28 and 29 were repeated 5 times in accordance with the same method as described in Example 30. The results of the fifth hydrogenation reactions are shown in Table 4.

TABLE 4

| Examples | Example No. in which the catalysts employed are prepared | Conversion of benzene (%) | Selectivity for cyclohexene (%) | Yield of cyclohexene (%) |
|---|---|---|---|---|
| Example 31 | 9 | 61.5 | 33.2 | 20.4 |
| Example 32 | 11 | 50.7 | 31.8 | 16.1 |
| Example 33 | 14 | 65.3 | 19.8 | 12.9 |
| Example 34 | 17 | 60.3 | 25.7 | 15.5 |
| Example 35 | 18 | 28.3 | 39.6 | 11.2 |

TABLE 4-continued

| Examples | Example No. in which the catalysts employed are prepared | Conversion of benzene (%) | Selectivity for cyclohexene (%) | Yield of cyclohexene (%) |
|---|---|---|---|---|
| Example 36 | 22 | 62.3 | 31.7 | 19.7 |
| Example 37 | 25 | 62.3 | 20.1 | 12.5 |
| Example 38 | 26 | 35.6 | 40.2 | 14.3 |
| Example 39 | 27 | 48.2 | 27.3 | 13.2 |
| Example 40 | 28 | 47.0 | 24.3 | 11.4 |
| Example 41 | 29 | 50.7 | 31.2 | 15.8 |

COMPARATIVE EXAMPLE 14

Using the same reaction system as in Comparative Example 7, the hydrogenation of benzene was repeated according to the same method as described in Example 30. In the second hydrogenation reaction, the conversion of benzene was 3.2%, the selectivity for cyclohexene was 72.2%, and the yield of cyclohexene was lowered to 2.2%.

After completion of the second hydrogenation reaction, most of the solid carrier of the catalyst was dissolved out, leaving black precipitates of ruthenium.

COMPARATIVE EXAMPLE 15

Using the same reaction system as in Comparative Example 13, the hydrogenation of benzene was repeated according to the same method as described in Example 30. In the second hydrogenation reaction, the conversion of benzene was 16.9%, the selectivity for cyclohexene was 38.3%, and the yield of cyclohexene was 6.5%. Further, in the third hydrogenation reaction, the conversion of benzene and the yield of cyclohexene were lowered to 6.8% and 3.5%, respectively, although the selectivity for cyclohexene was increased to 51.5

EXAMPLES 42 to 50

Hydrogenation reactions of benzene were carried out in substantially the same manner as in Examples 5 to 7, except that 1 g of an auxiliary compound as indicated in Table 5 given below was added to the reaction system and that the reaction time was changed as indicated in Table 5. The results are shown in Table 5.

TABLE 5

| Examples | Auxiliary compound | Reaction time (minutes) | Conversion of benzene (%) | Selectivity for cyclohexene (%) | Yield of cyclohexene (%) |
|---|---|---|---|---|---|
| Example 42 | Zinc chloride | 40 | 19.2 | 69.5 | 13.3 |
| Example 43 | Zinc chloride | 60 | 28.5 | 64.5 | 18.4 |
| Example 44 | Zinc chloride | 75 | 40.5 | 61.3 | 24.8 |
| Example 45 | Zinc oxide | 40 | 20.3 | 75.3 | 15.3 |
| Example 46 | Zinc oxide | 60 | 27.8 | 69.6 | 19.3 |
| Example 47 | Zinc oxide | 75 | 41.2 | 65.3 | 26.9 |
| Example 48 | Zinc hydroxide | 40 | 24.5 | 75.5 | 18.5 |
| Example 49 | Zinc hydroxide | 60 | 32.3 | 67.3 | 21.7 |
| Example 50 | Zinc hydroxide | 75 | 43.2 | 63.5 | 27.4 |

As is apparent from Table 5 and the data obtained in Examples 5 to 7, the addition of a zinc compound to the reaction system caused the rate of hydrogenation to be decreased. However, the yield of cyclohexene was increased when the conversions of benzene were substantially the same as each other.

EXAMPLE 51

A compound oxide was prepared as follows. 216.5 g of $La(NO_3)_3.6H_2O$ (special grade, manufactured and sold by Wako Pure Chemical Industry, Ltd., Japan) and 29.7 g of $Zn(NO_3)_2.6H_2O$ (special grade, manufactured and sold by Wako Pure Chemical Industry, Ltd., Japan) were dissolved in 200 ml of water to prepare a solution. The solution thus obtained was heated to 80° C. on a water bath. An aqueous sodium carbonate solution was added to the solution kept at 80° C. while stirring to adjust the pH value to 10, so that precipitates were formed in the solution. The thus formed precipitates were filtered, washed thoroughly with water, and then dried in vacuo (30 mmHg) at 80° C. for 6 hours and subjected to heat treatment at 500° C. for 6 hours in a stream of air. The obtained product was subjected to X-ray diffractometry. The X-ray diffraction pattern was obtained by using a recording X-ray diffractometer (RAD-IIIA manufactured and sold by Rigaku Corporation, Japan; 15 KV; 100 mA). From the X-ray diffraction pattern of the product, it was confirmed that the X-ray diffraction pattern was utterly different from those of lanthanum oxide and zinc oxide, and that the product was a compound oxide consisting of lanthanum oxide and zinc oxide. Part of the obtained double oxide was dissolved in nitric acid to prepare a homogeneous solution and then subjected to an emission spectroanalysis for determination of the atomic ratio of La to Zn with respect to the compound oxide using an inductively coupled plasma equipment (JY-38 PII, manufactured and sold by Seiko Denshi Kogyo K. K., Japan). As a result, it was found that the atomic ratio of La to Zn was 5:1.

Substantially the same procedures as in Example 1 were repeated to prepare a ruthenium catalyst, except that the above-obtained compound oxide was used as a solid carrier instead of $La_2O_3$. Thus, there was obtained a ruthenium catalyst consisting of the compound oxide and, supported thereon, 1 wt %, in terms of ruthenium element, of ruthenium component.

5 g of the above-obtained catalyst, 100 ml of benzene and 10 g of sodium hydroxide were charged into a stainless steel (SUS 316) autoclave (capacity: 1 liter) equipped with a stirrer, and the hydrogenation of benzene was carried out under a hydrogen pressure of 50 $Kg/cm^2G$ at a temperature of 175 ° C. for 30 minutes. The results are shown in Table 6 given below.

EXAMPLES 52 to 55

Solid carriers were prepared in substantially the same manner as in Example 51, except that the amounts of $La(NO_3)_3.6H_2O$ and $Zn(NO_3)_2.6H_2O$ were charged as indicated in Table 6 given below. The obtained products were subjected to X-ray diffractometry. As a result, it was found that when the atomic ratio of Zn to La was more than 1:1 the product was a mixture of zinc oxide and a compound oxide consiting of lanthanum oxide and zinc oxide.

Substantially the same procedures as in Example 51 were repeated to prepare ruthenium catalysts, except that the above-obtained products were used as solid carriers instead of the compound oxide used in Example 51. Thus, there were obtained ruthenium catalysts each containing 1 wt %, in terms of ruthenium element and based on the solid carrier, of ruthenium component.

Hydrogenation reactions of benzene were effected in substantially the same manner as in Example 51, except that the above-obtained catalysts were used instead of the catalyst used in Example 51. The results are shown in Table 6 given below.

TABLE 6

| Examples | Atmic ratio of Zn to La | Reaction time (minutes) | Conversion of benzene (%) | Selectivity for cyclohexene (%) | Yield of cyclohexene (%) |
| --- | --- | --- | --- | --- | --- |
| Example 51 | 1:5 | 30 | 62.8 | 54.9 | 34.5 |
| Example 52 | 1:0.3 | 49 | 62.0 | 60.4 | 37.4 |
| Example 53 | 1:1 | 60 | 64.5 | 56.0 | 36.4 |
| Example 54 | 1:3 | 87 | 60.3 | 61.2 | 36.9 |
| Example 55 | 1:9 | 7 | 64.3 | 30.2 | 19.4 |

EXAMPLES 56 and 57

Ruthenium catalysts were prepared in substantially the same manner as in Example 5, except that solid carriers as indicated in Table 7 given below were used instead of lanthanum oxide.

Hydrogenation reactions were carried out in substantially the same manner as in Example 5, except that the above-obtained catalyst were used instead of the catalyst used in Example 5 and that the reaction time was 30 min. The results are shown in Table 7.

TABLE 7

| Examples | Solid carrier | Reaction time (minutes) | Conversion of benzene (%) | Selectivity for cyclohexene (%) | Yield of cyclohexene (%) |
| --- | --- | --- | --- | --- | --- |
| Example 56 | lanthanum hydroxide | 30 | 36.8 | 64.2 | 23.6 |
| Example 57 | lanthanum carbonate | 30 | 36.2 | 54.8 | 19.8 |

EXAMPLE 58

$RuCl_3.3H_2O$ (manufactured and sold by Nippon Engelhard Ltd., Japan) was dissolved in water to obtain an aqueous solution containing 0.01 wt % of ruthenium. In 3,000 ml of the aqueous solution was dispersed 30 g of lanthanum oxide powder (manufactured and sold by Wako Pure Chemical Industries Ltd., Japan) to be used as a solid carrier. The resulting mixture was stirred for 3 hours and allowed to stand. The adsorption of ruthenium on lanthanum oxide was confirmed by the disappearance of the dark brown color of ruthenium. The mixture was then subjected to filtration. The obtained solid was dried in vacuo (20 mmHg) at 80° C. for 6 hours to obtain a dried powder.

20 g of the above-obtained powder was put in a pyrex tube having a diameter of 20 mm and placed in a tubular electric furnace. Nitrogen gas was flushed into the tube. The contents of the tube were heated to a temperature of 400° C. in a stream of nitrogen gas, then kept at 400° C. for 2 hours while passing hydrogen gas through the tube at a flow rate of 50 N l/hr, and cooled to room temperature in an atmosphere of nitrogen gas. The resultant catalyst was taken out of the tube. Thus, there was obtained a catalyst consisting of $La_2O_3$ and, supported thereon, 1 wt %, in terms of ruthenium element, of ruthenium component.

5 g of the above-obtained catalyst, 30 g of potassium hydroxide dissolved in 400 ml of water and 100 ml of benzene were put in a stainless steel (SUS316) autoclave (capacity: 1 liter) equipped with a stirrer. The atmosphere in the autoclave was replaced by nitrogen gas and then by hydrogen gas. The temperature of the contents was elevated to 155° C. while stirring. After elevation of the temperature, hydrogen gas was fed into the autoclave, and the contents were kept at 175° C. under a pressure of 50 kg/cm$^2$G for 10 minutes to effect a hydrogenation reaction.

Thereafter, the contents of the autoclave were cooled rapidly, and the organic layer was taken out of the autoclave and subjected to analysis by means of gas chromatography. As a result, it was found that the conversion of benzene was 28.5% and that the selectivity for cyclohexene was 74.2%. Beside the desired cyclohexene, there was observed formation of cyclohexane.

EXAMPLES 59 to 73

Ruthenium catalysts were prepared in substantially the same manner as in Example 58, except that solid carriers as indicated in Table 8 given below were used instead of lanthanum oxide. Hydrogenation reactions were carried out in substantially the same manner as in Example 58, except that the above-obtained catalysts were used instead of the catalyst used in Example 58. The results are shown in Table 8 together with the data obtained in Example 58.

TABLE 8

| Examples | Solid carrier | Reaction time (minutes) | Conversion of benzene (%) | Selectivity for cyclohexene (%) | Yield of cyclohexene (%) |
| --- | --- | --- | --- | --- | --- |
| Example 58 | $La_2O_3$ | 10 | 28.5 | 74.2 | 21.1 |
| Example 59 | $Tm_2O_3$ | 5 | 20.5 | 40.2 | 8.2 |
| Example 60 | $Yb_2O_3$ | " | 23.5 | 52.3 | 12.2 |
| Example 61 | $Tb_4O_7$ | " | 46.2 | 30.2 | 13.9 |
| Example 62 | $CeO_2$ | " | 20.1 | 51.2 | 10.2 |
| Example 63 | $Y_2O_3$ | 10 | 18.5 | 55.5 | 10.2 |
| Example 64 | $Lu_2O_3$ | " | 24.5 | 52.3 | 12.8 |
| Example 65 | $Sm_2O_3$ | 5 | 40.1 | 39.2 | 15.7 |
| Example 66 | $Dy_2O_3$ | " | 22.5 | 45.3 | 10.2 |
| Example 67 | $Nd_2O_3$ | " | 24.3 | 51.8 | 12.5 |
| Example 68 | $Pr_6O_{11}$ | " | 23.8 | 49.7 | 11.8 |
| Example 69 | $Eu_2O_3$ | " | 23.6 | 52.3 | 12.3 |
| Example 70 | $Sc_2O_3$ | 10 | 19.5 | 61.8 | 12.0 |
| Example 71 | $Gd_2O_3$ | " | 35.2 | 49.3 | 17.3 |
| Example 72 | $Ho_2O_3$ | " | 30.2 | 45.2 | 13.6 |

TABLE 8-continued

| Examples | Solid carrier | Reaction time (minutes) | Conversion of benzene (%) | Selectivity for cyclohexene (%) | Yield of cyclohexene (%) |
|---|---|---|---|---|---|
| Example 73 | Er$_2$O$_3$ | " | 38.2 | 43.6 | 16.6 |

EXAMPLES 74 to 77

In a stainless steel (SUS316) autoclave (capacity: 1 liter) equipped with a stirrer were charged 3.5 g of the catalyst as prepared in Example 58, 70 mg of zinc oxide and 7 g of sodium hydroxide dissolved in 280 g of water. The atmosphere in the autoclave was replaced by nitrogen and then by hydrogen. The temperature of the contents in the autoclave were elevated to 150° C. while stirring. After elevation of the temperature, 140 ml of benzene was charged into the autoclave. The hydrogenation of benzene was effected at 150° C. under a hydrogen pressure of 50 kg/cm$^2$G for periods of time as given in Table 9. The results are shown in Table 9.

TABLE 9

| Examples | Reaction time (minutes) | Conversion of benzene (%) | Selectivity for cyclohexene (%) | Yield of cyclohexene (%) |
|---|---|---|---|---|
| 74 | 15 | 14.2 | 90.2 | 12.8 |
| 75 | 30 | 27.6 | 85.3 | 23.5 |
| 76 | 45 | 41.4 | 78.2 | 32.4 |
| 77 | 60 | 52.3 | 70.4 | 36.8 |

EXAMPLE 78 to 92

Hydrogenation of benzene were carried out in substantially same manner as in Example 74, except that the catalysts prepared in Examples 59 to 73 were used instead of the catalyst used in Example 74 and that the reaction time was changed as indicated in Table 10 given below. The results are shown in Table 10.

TABLE 10

| Examples | Example No. in which the catalysts employed are prepared | Reaction time (minutes) | Conversion of benzene (%) | Selectivity for cyclohexene (%) | Yield of cyclohexene (%) |
|---|---|---|---|---|---|
| Example 78 | 59 | 15 | 21.5 | 67.4 | 14.5 |
| Example 79 | 60 | " | 22.3 | 62.3 | 13.9 |
| Example 80 | 61 | " | 43.5 | 35.4 | 15.4 |
| Example 81 | 62 | " | 21.3 | 63.5 | 13.5 |
| Example 82 | 63 | 30 | 20.7 | 68.2 | 14.1 |
| Example 83 | 64 | 15 | 27.5 | 58.3 | 16.0 |
| Example 84 | 65 | " | 38.4 | 53.2 | 20.4 |
| Example 85 | 66 | " | 26.2 | 60.5 | 15.8 |
| Example 86 | 67 | " | 27.3 | 62.3 | 17.0 |
| Example 87 | 68 | " | 25.7 | 58.6 | 15.1 |
| Example 88 | 69 | " | 24.5 | 65.3 | 16.0 |
| Example 89 | 70 | 20 | 20.9 | 70.4 | 14.7 |
| Example 90 | 71 | " | 28.4 | 68.6 | 19.5 |
| Example 91 | 72 | " | 30.1 | 65.3 | 19.6 |
| Example 92 | 73 | " | 32.3 | 67.8 | 21.9 |

EXAMPLE 93

A compound oxide consisting of lanthanum oxide and aluminum oxide was prepared as follows. 216.5 g of La(NO$_3$)$_3$.6H$_2$O (special grade, manufactured and sold by Wako Pure Chemical Industry, Ltd., Japan) and 37.5 of Al(NO$_3$)$_3$.9H$_2$O (special grade, manufactured and sold by Wako Pure Chemical Industry, Ltd., Japan) were dissolved in 200 ml of water to prepare a solution. The solution thus obtained was heated to 80° C. on a water bath. An aqueous sodium carbonate solution was added to the solution kept at 80° C. while stirring to adjust the pH value to 10, so that precipitates were formed in the solution. The thus formed precipitates were filtered, washed thoroughly with water, and then dried in vacuo (30 mmHg) at 80° C. for 6 hours and subjected to heat treatment at 500° C. for 6 hours in a stream of air. The obtained product was subjected to X-ray diffractometry. The X-ray diffraction pattern was obtained by using a recording X-ray diffractometer (RAD-IIIA) manufactured and sold by Rigaku corporation, Japan; 15 KV; 100 mA). From the X-ray diffraction pattern of the product, it was confirmed that the X-ray diffraction pattern was utterly different from those of lanthanum oxide and aluminum oxide, and that the product was a compound oxide consisting of lanthanum oxide and aluminum oxide. Part of the obtained compound oxide was dissolved in nitric acid to prepare a homogeneous solution and then subjected to an emission spectroanalysis for determination of the atomic ratio of La to Al with respect to the compound oxide using an inductively coupled plasma equipment (JY-38PII, manufacture and sold by Seiko Denshi Kogyo K. K., Japan). As a result, it was found that the atomic ratio of La to Al was 5:1.

Substantially the same procedures as in Example 58 were repeated to prepare a ruthenium catalyst, except that the above-obtained compound oxide was used as a solid carrier instead of the compound oxide used in Example 58. Thus, there was obtained a ruthenium catalyst consisting of the compound oxide and, supported thereon, 1 wt %, in terms of ruthenium element, of ruthenium component.

The hydrogenation of benzene was effected in substantially the same manner as in Example 77, except that the above-obtained catalyst was used instead of the catalyst used in Example 77. The results are shown in Table 11 given below.

EXAMPLE 94

Substantially the same procedures as in Example 58 were repeated to prepare a ruthenium catalyst, except that the double oxide prepared in Example 93 was used as solid carrier instead of the solid carrier used in Example 58.

The hydrogenation of benzene was effected in substantially the same manner as in Example 77, except that the above-obtained catalyst was used instead of the catalyst used in Example 77. The results are shown in Table 11 given below.

TABLE 11

| Examples | Conversion of benzene (%) | Selectivity for cyclohexene (%) | Yield of cyclohexene (%) |
|---|---|---|---|
| 93 | 55.6 | 64.0 | 35.6 |
| 94 | 48.5 | 74.5 | 36.1 |

EXAMPLES 95 TO 97

The hydrogenation of a monocyclic aromatic hydrocarbon was effected in substantially the same manner as in Example 74, except that the catalyst prepared in Example 58 was used instead of the catalyst used in Example 74 and that monocyclic aromatic hydrocarbons as indicated in Table 12 were used instead of benzene. The results are shown in Table 12.

TABLE 12

| Examples | Monocyclic aromatic hydrocarbon | Reaction time (min) | Conversion (%) | Selectivity for cycloolefins (total) | Each isomer of the cycloolefins | |
|---|---|---|---|---|---|---|
| 95 | C₆H₅—CH₃ | 50 | 32.3 | 75.4% | (72%) | (28%) |
| 96 | H₃C—C₆H₄—CH₃ | 80 | 28.3 | 72.3% | (35%) | (65%) |
| 97 | C₆H₅—CH₂.CH₃ | 75 | 27.7 | 78.6% | (76%) | (24%) |

What is claimed is:

1. A process for producing a cycloolefin which comprises partially hydrogenating a monocyclic aromatic hydrocarbon in the presence of water, an alkaline agent and a ruthenium catalyst composed of a solid carrier and a ruthenium component supported thereon, said solid carrier consisting essentially of at least one rare earth element compound, said rare earth element being selected from the group consisting of La, Ce, Pr, Nd, Pm, Sm, Eu, Gd, Tb, Dy, Ho, Er, Tm, Yb, Lu, Sc and Y, said carrier supporting thereon 0.01 to 10 wt. % of said ruthenium component, based on said solid carrier.

2. A process according to claim 1, wherein said rare earth element is at least one member selected from the group consisting of Sc, La, Ce, Tb and Yb.

3. A process according to claim 1, wherein said rare earth element is La.

4. A process according to claim 1, wherein said rare earth element compound is at least one member selected from the group consisting of oxides, hydroxides, carbonates and phosphates of a rare earth element.

5. A process according to claim 1, wherein said rare earth element compound is at least one member selected from the group consisting of oxides and hydroxides of a rare earth element.

6. A process according to claim 1, wherein said rare earth element compound is at least one member selected from the group consisting of oxides and hydroxides of La.

7. A process according to claim 1, wherein said ruthenium catalyst has been treated with a reducing agent, to the extent that part or all of said ruthenium component is present in the form of metallic ruthenium.

8. A process according to claim 7, wherein said reducing agent is hydrogen.

9. A process according to claim 7, wherein said reducing agent is hydrogen and said treatment is effected in the vapor phase.

10. A process according to claim 1, wherein said carrier supports thereon, 0.1 to 5 wt % of said ruthenium component, based on said solid carrier.

11. A process according to claim 1, wherein said monocyclic aromatic hydrocarbon is selected from the group consisting of benzene, toluene, o-xylene, m-xylene, p-xylene and ethylbenzene.

12. A process according to claim 1, wherein said monocyclic aromatic hydrocarbon is benzene.

13. A process according to claim 1, wherein said water is present in an amount 0.01 to 100 times by weight of the amount of said monocyclic aromatic hydrocarbon.

14. A process according to claim 1, wherein said water is present in an amount 0.5 to 20 times by weight of the amount of said monocyclic aromatic hydrocarbon.

15. A process according to claim 1, wherein said alkaline agent is at least one member selected from the group consisting of hydroxides, oxides and carbonates of metals of the Groups Ia and IIa of the Periodic Table, ammonia and organic bases.

16. A process according to claim 15, wherein said alkaline agent is at least one member selected from the group consisting of hydroxides, oxides and carbonates of Li, Na, K, Rb or Cs.

17. A process according to claim 1, wherein said water and said alkaline agent constitute an aqueous solution which comprises 0.01 to 10 mol/liter of said alkaline agent.

18. A process according to claim 1, wherein said water and said alkaline agent constitute an aqueous solution which comprises 0.1 to 5 mol/liter of said alkaline agent.

19. A process according to claim 1, wherein said partial hydrogenation of a monocyclic aromatic hydrocarbon is effected in the copresence of an auxiliary compound selected from the group consisting of compounds of Zn and Al.

20. A process according to claim 19, wherein said auxiliary compound is at least one member selected from the group consisting of chlorides, bromides, fluorides, sulfates, nitrates, phosphates, carbonates, organic acid salts, oxides and hydroxides of Zn or Al.

21. A process according to claim 19, wherein said auxiliary compound is a compound of Zn.

22. A process according to claim 21, said compound of Zn is selected from the group consisting of an oxide and hydroxide of Zn.

23. A process according to claim 19, wherein said auxiliary compound is used in an amount of 0.01 to 20 mol %, in terms of ruthenium element, based on the amount of the ruthenium component.

24. A process according to claim 1, wherein said partial hydrogenation of a monocyclic aromatic hydrocarbon is effected at a temperature of 20° to 250° C.

25. A process according to claim wherein said temperature is 100° to 200° C.

26. A process according to claim 1, wherein said partial hydrogenation of a monocyclic aromatic hydrocarbon is effected under a hydrogen pressure of 1 to 200 kg/cm$^2$G.

27. A process according to claim wherein said hydrogen pressure is 10 to 100 kg/cm$^2$G.

28. A process according to claim 1, wherein 0.001 to 50 wt % of said ruthenium catalyst is present, based on the amount of said monocyclic aromatic hydrocarbon.

29. A process according to claim 28, wherein 0.01 to 20 wt% of said ruthenium catalyst is present, based on the amount of said monocyclic aromatic hydrocarbon.

* * * * *

UNITED STATES PATENT AND TRADEMARK OFFICE
CERTIFICATE OF CORRECTION

PATENT NO. : 4,678,861
DATED : July 7, 1987
INVENTOR(S) : OSAMU MITSUI

It is certified that error appears in the above-identified patent and that said Letters Patent is hereby corrected as shown below:

Claim 25, line 1, after "claim" insert --24--.

Claim 27, line 1, after "claim" insert --26--.

Signed and Sealed this

Fifteenth Day of March, 1988

Attest:

DONALD J. QUIGG

Attesting Officer     Commissioner of Patents and Trademarks